(12) United States Patent
Botchkareva et al.

(10) Patent No.: US 7,727,516 B2
(45) Date of Patent: Jun. 1, 2010

(54) REDUCTION OF HAIR GROWTH

(75) Inventors: Natalia Botchkareva, Sharon, MA (US); Douglas Shander, Acton, MA (US)

(73) Assignee: The Procter & Gamble Company, Cincinnati, OH (US)

(*) Notice: Subject to any disclaimer, the term of this patent is extended or adjusted under 35 U.S.C. 154(b) by 448 days.

(21) Appl. No.: 11/709,616

(22) Filed: Feb. 22, 2007

(65) Prior Publication Data

US 2008/0195183 A1    Aug. 14, 2008

Related U.S. Application Data

(60) Provisional application No. 60/777,888, filed on Feb. 28, 2006.

(51) Int. Cl.
*A61K 7/06* (2006.01)
(52) U.S. Cl. .................. 424/74; 514/564; 606/89; 607/89
(58) Field of Classification Search ............ 606/9; 514/564; 424/74
See application file for complete search history.

(56) References Cited

U.S. PATENT DOCUMENTS

| | | | |
|---|---|---|---|
| 3,821,221 A | 6/1974 | Podesva et al. | |
| 4,720,489 A | 1/1988 | Shander | |
| 4,885,289 A | 12/1989 | Breuer et al. | |
| 5,095,007 A | 3/1992 | Ahluwalia | |
| 5,096,911 A | 3/1992 | Shander et al. | |
| 5,132,293 A | 7/1992 | Shander et al. | |
| 5,143,925 A | 9/1992 | Shander et al. | |
| 5,279,819 A | 1/1994 | Hayes | |
| 5,283,924 A | 2/1994 | Kaminski et al. | |
| 5,300,290 A | 4/1994 | Spencer | |
| 5,320,842 A | 6/1994 | Spencer | |
| 5,326,556 A | 7/1994 | Barnet et al. | |
| 5,328,686 A | 7/1994 | Shander et al. | |
| 5,340,581 A | 8/1994 | Tseng et al. | |
| 5,357,990 A | 10/1994 | Suhonen et al. | |
| 5,364,885 A | 11/1994 | Ahluwalia et al. | |
| 5,411,991 A | 5/1995 | Shander et al. | |
| 5,440,090 A | 8/1995 | Davis et al. | |
| 5,468,476 A | 11/1995 | Ahluwalia et al. | |
| 5,475,763 A | 12/1995 | Kaufman et al. | |
| 5,500,211 A | 3/1996 | George et al. | |
| 5,514,671 A | 5/1996 | Lyon et al. | |
| 5,554,608 A | 9/1996 | Ahluwalia et al. | |
| 5,565,206 A | 10/1996 | Spencer | |
| 5,626,154 A | 5/1997 | Rogers et al. | |
| 5,641,508 A * | 6/1997 | Li et al. ............ | 424/450 |
| 5,647,866 A * | 7/1997 | Zaias et al. ............ | 606/9 |
| 5,648,394 A | 7/1997 | Boxall et al. | |
| 5,652,273 A | 7/1997 | Henry et al. | |
| 5,653,971 A | 8/1997 | Badin et al. | |
| 5,669,916 A * | 9/1997 | Anderson ............ | 606/133 |
| 5,674,477 A | 10/1997 | Ahluwalia | |
| 5,680,876 A | 10/1997 | Hasham et al. | |
| 5,713,131 A | 2/1998 | Rogers et al. | |
| 5,720,941 A | 2/1998 | Spencer | |
| 5,723,132 A | 3/1998 | Tseng et al. | |
| 5,728,736 A | 3/1998 | Shander et al. | |
| 5,776,442 A | 7/1998 | Ahluwalia | |
| 5,824,663 A | 10/1998 | Brockett | |
| 5,824,665 A | 10/1998 | Henry et al. | |
| 5,836,769 A | 11/1998 | Spencer | |
| 5,840,752 A | 11/1998 | Henry et al. | |
| 5,843,413 A | 12/1998 | Causton et al. | |
| 5,851,551 A | 12/1998 | Tseng et al. | |
| 5,871,479 A * | 2/1999 | Furumoto et al. ............ | 606/9 |
| 5,871,715 A | 2/1999 | Singh | |
| 5,902,574 A | 5/1999 | Stoner et al. | |
| 5,906,834 A | 5/1999 | Tseng | |
| 5,908,867 A | 6/1999 | Henry et al. | |
| 5,939,458 A | 8/1999 | Henry et al. | |
| 5,941,256 A | 8/1999 | Guay et al. | |
| 5,956,848 A | 9/1999 | Tseng et al. | |
| 5,958,946 A | 9/1999 | Styczynski et al. | |
| 5,962,466 A | 10/1999 | Styczynski et al. | |
| 5,967,153 A | 10/1999 | Mitha | |
| 5,998,431 A | 12/1999 | Tseng et al. | |
| 6,020,006 A * | 2/2000 | Styczynski et al. ............ | 424/646 |
| 6,037,326 A | 3/2000 | Styczynski et al. | |
| 6,060,471 A | 5/2000 | Styczynski et al. | |
| 6,093,748 A | 7/2000 | Ahluwalia et al. | |
| 6,121,269 A | 9/2000 | Henry et al. | |

(Continued)

FOREIGN PATENT DOCUMENTS

EP    0837760 B1    2/1999

(Continued)

OTHER PUBLICATIONS

Bodo et al., A Hot New Twist to Hair Biology, Apr. 2005, American Journal of Pathology, vol. 166, No. 4, pp. 985-998.*

(Continued)

*Primary Examiner*—Henry M Johnson, III
*Assistant Examiner*—Jeffrey B Lipitz
(74) *Attorney, Agent, or Firm*—Fish & Richardson P.C.

(57) ABSTRACT

A method of reducing hair growth includes topical application of a TRPM8 and/or a TRPA1 agonist, alone or in conjunction with heat.

20 Claims, No Drawings

U.S. PATENT DOCUMENTS

| | | | |
|---|---|---|---|
| 6,145,516 A | 11/2000 | Guay et al. | |
| 6,146,687 A | 11/2000 | Desai | |
| 6,165,456 A | 12/2000 | Barnet et al. | |
| 6,182,365 B1 | 2/2001 | Tseng et al. | |
| 6,185,822 B1 | 2/2001 | Tseng et al. | |
| 6,218,435 B1 | 4/2001 | Henry et al. | |
| 6,235,737 B1 | 5/2001 | Styczynski et al. | |
| 6,239,170 B1 | 5/2001 | Ahluwalia et al. | |
| 6,247,930 B1 | 6/2001 | Chiang et al. | |
| 6,248,751 B1 | 6/2001 | Ahluwalia et al. | |
| 6,273,883 B1 * | 8/2001 | Furumoto | 606/9 |
| 6,273,884 B1 | 8/2001 | Altshuler et al. | |
| 6,298,558 B1 | 10/2001 | Tseng et al. | |
| 6,299,865 B1 | 10/2001 | Styczynski et al. | |
| 6,386,778 B1 | 5/2002 | Guay et al. | |
| 6,414,017 B2 | 7/2002 | Ahluwalia et al. | |
| 6,415,800 B2 | 7/2002 | Poisson et al. | |
| 6,442,839 B1 | 9/2002 | Tseng et al. | |
| 6,475,553 B2 | 11/2002 | Guay et al. | |
| 6,569,411 B2 | 5/2003 | Frater et al. | |
| 6,594,904 B1 | 7/2003 | Tseng et al. | |
| 6,622,943 B2 | 9/2003 | Poisson et al. | |
| 6,743,419 B1 | 6/2004 | Shander et al. | |
| 6,743,822 B2 | 6/2004 | Styczynski et al. | |
| 6,916,468 B2 | 7/2005 | Lasota | |
| 6,919,348 B2 | 7/2005 | Wei | |
| 6,944,952 B1 | 9/2005 | Tseng | |
| 2001/0013352 A1 | 8/2001 | Poisson et al. | |
| 2002/0020065 A1 | 2/2002 | Tseng | |
| 2002/0081556 A1 | 6/2002 | Tseng et al. | |
| 2003/0049209 A1 | 3/2003 | Tseng et al. | |
| 2003/0053980 A1 | 3/2003 | Dodd et al. | |
| 2003/0096871 A1 * | 5/2003 | Styczynski et al. | 514/564 |
| 2003/0199584 A1 | 10/2003 | Ahluwalia et al. | |
| 2003/0207904 A1 * | 11/2003 | Wei | 514/269 |
| 2004/0009142 A1 * | 1/2004 | Zambaux et al. | 424/74 |
| 2004/0018167 A1 | 1/2004 | Lasota | |
| 2004/0134010 A1 | 7/2004 | Tseng et al. | |
| 2004/0141935 A1 | 7/2004 | Styczynski et al. | |
| 2004/0192778 A1 | 9/2004 | Jardien et al. | |
| 2004/0228820 A1 * | 11/2004 | Elliott et al. | 424/70.11 |
| 2005/0112075 A1 | 5/2005 | Hwang et al. | |
| 2005/0112084 A1 | 5/2005 | O'Grady et al. | |
| 2005/0209193 A1 * | 9/2005 | Keller | 514/64 |
| 2005/0249685 A1 | 11/2005 | Botchkareva et al. | |

FOREIGN PATENT DOCUMENTS

| | | |
|---|---|---|
| EP | 0790883 B1 | 3/1999 |
| EP | 0837759 B1 | 3/1999 |
| EP | 1494637 A2 | 1/2005 |
| WO | WO 9613360 A1 | 5/1996 |
| WO | WO 9702116 A1 | 1/1997 |
| WO | WO 9702117 A1 | 1/1997 |
| WO | WO 02052978 A2 | 7/2002 |
| WO | WO 03086331 A2 | 10/2003 |
| WO | WO 2004012694 A1 | 2/2004 |
| WO | WO 2004064749 A2 | 8/2004 |
| WO | WO 2004087083 A2 | 10/2004 |
| WO | WO 2005051335 A1 | 6/2005 |
| WO | WO 2005051341 A2 | 6/2005 |
| WO | WO 2005105023 A1 | 11/2005 |
| WO | WO 2005089206 | 6/2006 |

OTHER PUBLICATIONS

Mark B. Erman, "Cooling Agents and Skin Care Applications", www.thecosmeticsite.com; Cosmetics & Toiletries Magazine vol. 120, No. 5/May 2005.

H. J. Behrendt, T. Germann, C. Gillen, H. Hatt & R. Jostock, "Characterization of the mouse cold-menthol receptor TRPM8 and vanilloid receptor type-1 VR1 using a fluorometric imaging plate reader (FLIPR) assay"; British Journal of Phamacology, vol. 141 pp. 737-745.

Joao B. Calixtro, Candida A.L. Kassuya, Eunice Andre, Juliano Ferreira, "Contribution of natural products to the discovery of the transient receptor potential (TRP) channels family and their functions", Pharmacology & Therapeutics 106 (2005); pp. 179-208.

David D. Mckemy, "How cold is it? TRPM8 and TRPA1 in the molecular logic of cold sensation", Molecular Pain, 2005, 1:16.

Cayman Chemicals Product Information of Icilin, Jul. 13, 2005.

Biomol International Product Data of Icilin, no date.

* cited by examiner

SEQUENCE LISTING

```
<160> NUMBER OF SEQ ID NOS: 4

<210> SEQ ID NO 1
<211> LENGTH: 24
<212> TYPE: DNA
<213> ORGANISM: Homo sapien

<400> SEQUENCE: 1
tcatggtcca acagaacaca tggc                                          24

<210> SEQ ID NO 2
<211> LENGTH: 24
<212> TYPE: DNA
<213> ORGANISM: Homo sapien

<400> SEQUENCE: 2
gcatgacagg catggtacag tgtt                                          24

<210> SEQ ID NO 3
```

```
-continued
<211> LENGTH: 24
<212> TYPE: DNA
<213> ORGANISM: Homo sapien

<400> SEQUENCE: 3
tcctctccat ctggcagcaa agaa                                              24

<210> SEQ ID NO 4
<211> LENGTH: 24
<212> TYPE: DNA
<213> ORGANISM: Homo sapien

<400> SEQUENCE: 4
attgtggctc agaagaagcg caac                                              24
```

REDUCTION OF HAIR GROWTH

CROSS REFERENCE TO RELATED APPLICATION

This application claims the benefit of U.S. Provisional Application Ser. No. 60/777,888 filed on Feb. 28, 2006.

BACKGROUND OF THE INVENTION

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

The transient receptor potential (TRP) family of ion channels comprises more than 30 cation channels, and can be divided into seven main subfamilies: TRPC, TRPV, TRPM, TRPP, TRPML, TRPA, and the TRPN. Two members of two distinct subfamilies of TRP channels have been identified as being responsible for cold sensation: TRPM8 and TRPA1.

Transient Receptor Potential Melastatin-8 (TRPM8) belongs to the melastatin subfamily of TRP ion channels (Tominaga M. et al. (2004) *J. Neurobiol.* 61(1):3-12). TRPM8 is a Ca(2+)-permeable nonselective cation channel that mediates a direct influx of Ca(2+) ions in response to specific stimuli. It is activated by cold (temperatures below 24° C.) and by cooling compounds, such as menthol and icilin (Tsavaler et al. (2001) *Cancer Res.* 61(9):3760-9; McKemy et al. (2002) *Nature* 416:52-8; Peier et al. (2002) *Cell* 108(5):705-15). The TRPM8 channel is expressed in a subset of temperature-sensing small dorsal root and trigeminal ganglion neurons (McKemy et al. (2002) supra; Peier et al. (2002) supra; Babes et al. (2004) *Eur. J. Neurosci.* 20(9):2276-82; Nealen et al. (2003) *J. Neurophysiol.* 90(1):515-20). The trigeminal ganglion neurons supply sensory nerves for facial skin areas above the mouth, the area of the lower jaw, as well as above the forehead and around the eye. Therefore, TRPM8 has been implicated in sensing cold temperatures at mammalian thermoreceptor nerve endings. In addition to its presence on sensory neurons, functional TRPM8 receptor has also been identified on various non-neuronal cell types. TRPM8 mRNA expression was reported at moderate levels in normal prostate tissue and appears to be elevated in prostate cancer, where it involves in a number of Ca(2+)-dependent processes, including proliferation and apoptosis (Thebault et al, 2005) *J Biol Chem* 280(47):39423-35). It is also expressed in a number of primary tumors of breast, colon, lung, and skin origin (Tsavaler et al. (2001) supra).

Another ion channel, transient receptor potential channel ankyrin-repeat 1 (TRPA1) also referred to as ankyrin-like protein 1 (ANKTM1) receptor is activated by cold temperatures (below 18° C.), cinnamaldehyde, allicin, eugenol, gingerol, and methyl salicylate, and similar to TRPM8, by icilin. TRPA1 is expressed in a subset of sensory neurons expressing nociceptive markers, such as TRPV1, calcitonin gene related peptide (CGRP) and substance P (Story et al. (2003) *Cell* 112:819-829). It has also been reported to be expressed in cultured fibroblasts, where it is down-regulated after fibroblast oncogenic transformation (Jaquemar et al. (1999) *J. Biol. Chem.* 274:7325-7333).

SUMMARY OF THE INVENTION

In one aspect, the invention provides a method (typically a cosmetic method) of reducing unwanted mammalian (preferably human) hair growth. The method includes applying a composition including one or more cold receptor agonists, e.g., an agonist of Transient Receptor Potential Melastatin-8 (TRPM8) and/or an agonist of transient receptor potential channel ankyrin-repeat 1 (TRPA1) to an area of skin. The unwanted hair growth may be undesirable from, e.g., a cosmetic standpoint.

TRPM8 and/or TRPA1 agonists include compounds that activate at least one activity of one or more hair follicle TRPM8(s) and/or TRPA1(s) (e.g., one or more TRPM8(s) and/or TRPA1(s)) by strongly interacting with the TRPM8(s) and/or TRPA1(s); compounds that increase the levels and/or expression of one or more TRPM8(s) and/or TRPA1(s) in hair follicles; and/or compounds that increase the expression of one or more TRPM8 and/or TRPA1 mRNA's in hair follicles. "Strongly interacts" means a compound binds or preferentially binds to the TRPM8(s) and/or TRPA1(s). The compound can be selected, for example, from one of the types of compounds discussed below. Exemplary TRPM8 agonists include terpenes, e.g., cyclic terpenes (e.g., menthol or menthyl lactate), WS-3, cooling agent 10, Frescolat MGA, and Frescolat ML. The TRPM8 agonist may also be a TRPA 1 agonist, for example, icilin and eugenol. Other exemplary TRPA1 agonists include gingerol, methyl salicylate, allicin and cinnamaldehyde. Additional examples of TRPM8 and/or TRPA1 agonists are described herein.

In one embodiment, the composition consists essentially of a TRPM8 or a TRPA1 agonist, e.g., a composition having a TRPM8 or a TRPA1 agonist as the only active hair growth inhibitor. In other embodiments, the composition does not include one or more of: alpha-difluoromethylornithine (DFMO), a heat shock protein inhibitor, a compound that promotes apoptosis, or a combination thereof. In yet another embodiment, the composition does not include a terpene, e.g., menthol. In other embodiments, the composition includes 25% or higher of the TRPM8 and/or TRPA1 agonist by weight.

In other embodiments, the method includes a composition that includes one or more agonist(s) of TRPM8 and/or a TRPA1. In one embodiment, the agonist activates a TRPM8 and a TRPA1; for example, the agonist is icilin, which binds to and activates both channels. In other embodiments, a combination of one or more agonists selective for TRPM8 or TRPA1 is used.

Typically, in practicing the methods described herein, the composition will also include a dermatologically or cosmetically acceptable vehicle.

In another embodiment, the method further includes treating the area of skin with heat, a chemical depilatory (including, e.g., one or more hair growth reducing agents as described herein), or other methods of hair removal (including, one or more of, e.g., shaving, waxing, mechanical epilation, or electrolysis). In one embodiment, the heat depilatory treatment includes heating the area of skin with, for example, a laser or flashlamp. Typically, the heating is applied within ten, seven, five days, and more typically within three, two days or one day of, or simultaneously with, applying the composition. The appropriate time period depends on the specific agonist, and could be as short as one day. Treatment can even be simultaneous. Typically, the composition is applied multiple times and heating is performed within seven days, and more preferably within three, two days or one day, or simultaneously with, one of the applications. In other embodiments, the TRPM8 and/or TRPA1 agonist(s) enhances the efficacy of thermal-mediated hair inhibition and/or reduces the fluency of photothermal devices. For example, the energy output of the light and/or photothermal device can be reduced to about 10 to 30 J/cm2, more typically, about 1 to 3 J/cm2.

In other embodiments, the composition including the TRPM8 and/or TRPA1 agonist(s) is applied to the skin prior to, during, or after, application to the skin of a chemical depilatory or other methods of hair removal, e.g., waxing. For example, the composition can be applied once or multiple times and waxing is performed within seven days, and more preferably within three, two days or one day, or simultaneously with, one of the applications. The composition can also be applied after hair removal, e.g., waxing, thus providing an additional advantage of ameliorating the pain associated with hair removal. In some embodiments, the TRPM8 and/or TRPA1 agonist(s) decreases one or more undesirable effects induced by the heat, chemical, or other methods of depilation, including pain transmission, irritation and/or inflammation.

The present invention also relates to topical (e.g., cosmetic) compositions comprising a dermatologically or cosmetically acceptable vehicle and a cold receptor agonist, e.g., a TRPM8 and/or TRPA1 agonist as described herein, or a composition thereof. In addition, the present invention relates to the use of a cold receptor agonist, e.g., a TRPM8 and/or TRPA1 agonist as described herein, for the manufacture of a topical composition (e.g., a composition as described herein). Embodiments of these aspects of the invention may include one or more of the features discussed above.

Specific compounds mentioned herein include both the compound itself and pharmaceutically acceptable salts thereof.

Other features and advantages of the invention will be apparent from the detailed description, and from the claims.

DETAILED DESCRIPTION OF THE INVENTION

An example of a composition includes a cold receptor agonist, e.g., a TRPM8 and/or TRPA1 agonist, in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or solution. The composition may also be in the form of a shaving preparation or an aftershave. The vehicle itself can be inert or it can possess cosmetic, physiological and/or pharmaceutical benefits of its own.

Examples of TRPM8 agonists include terpenes, e.g., cyclic terpenes, such as menthol and menthyl lactate (Frescolat ML). Terpenes are a class of organic compounds found in essential oils and have been employed as fragrances, flavorings and medicines. A terpene refers to a compound that is based on an isoprene unit ($C_5H_8$) and can be classified based on the number of isoprenoid units that they contain. For example, a monoterpene consists of two isoprene units (C10), sesquiterpenes have three (C15) and diterpenes have four (C20). A commonly used terpene is menthol, which has been incorporated into inhalation and emollient preparations. Other examples of terpenes include eucalyptol (1,8-cineole), geraniol, nerolidol, menthone, cineole, terpineol, D-limonene, linalool, pulegol (e.g., isopulegol) and carvacrol. Other examples of terpene and non-terpene TRPM8 agonists include Trans-p-menthane-3,8-diol, cis-p-menthane-3,8-diol, L-carvone (Spearmint oil), N,2,3-trimethyl-2-isopropylbutanamide (WS-23), N-ethyl paramenthane-3-carboxamide (WS-3), menthone glycerin acetal (Frescolat MGA), menthoxypropanediol (Cooling agent 10), Coolact P, PMD-38, monomenthyl succinate (Physcool), monomenthyl glutarate and hydroxycitronellal. (See, for example, WO 2005/089206; Behrendt, H-J. et al. (2004) *British Journal of Pharmacology* 141:737-745; Calixto, J. B. et al. (2005) *Pharmacology & Therapeutics* 106:179-208 Erman, M. B. et al. (2005) *Cosmetics & Toiletries* 120(5):105-118, the contents of all of which are incorporated herein by reference).

Examples of agonists that bind to and activate TRPM8 and TRPA1 include eugenol, icilin and analogs thereof, e.g., icilin-like compounds. Icilin, 1-(2-Hydroxyphenyl)-4-(3-nitrophenyl)-1,2,3,6-tetrahydropyrimidin-2-one (CAS No. 36945-98-9) has a chemical structure as depicted below:

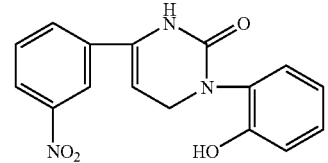

Icilin-like compounds typically have a 1-[R1-phenyl] 4-[R2-phenyl]-1,2,3,6-tetrahydropyrimidine-2-one general chemical structure as shown below, wherein R1 is typically chosen from one or more of hydroxy, chloro, fluoro, alkyl (with about 2 to about 4 carbon atoms), acetoxy, or trifluoromethyl; and R2 is typically chosen from one or more of nitro, chloro, fluoro, alkyl (with about 2 to 4 carbons), or trifluoromethyl.

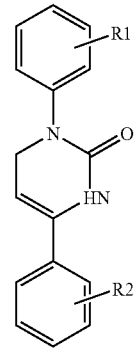

Methods suitable for preparing icilin and icilin-like compounds are described in U.S. Pat. No. 3,821,221 and U.S. Pat. No. 6,919,348, the contents of both of which are incorporated herein by reference.

Examples of TRPA-1 agonists include gingerol; methyl salicylate (Wintergreen oil); isothiocyanate compounds (e.g., allicin or allyl isothiocyanate (Mustard oil), as well as benzyl, phenylethyl, isopropyl, and methyl isothiocyanate); cinnamaldehyde (Cinnamon oil); and $\Delta^9$-tetrahydrocannabinol. Methods for synthesizing and testing the TRPA1 agonists disclosed herein, as well as analogs thereof, are known in the art and are described, for example, in WO 2005/089206 and Calixto, J. B. et al. (2005) supra, the contents of which is hereby incorporated by reference.

The composition may include more than one TRPM8 and/or TRPA1 agonists. The composition also may include one or more other types of hair growth reducing agents, such as those described in U.S. Pat. No. 4,720,489; U.S. Pat. No. 4,885,289; U.S. Pat. No. 5,095,007; U.S. Pat. No. 5,096,911; U.S. Pat. No. 5,132,293; U.S. Pat. No. 5,143,925; U.S. Pat. No. 5,328,686; U.S. Pat. No. 5,364,885; U.S. Pat. No. 5,411,991; U.S. Pat. No. 5,440,090; U.S. Pat. No. 5,468,476; U.S. Pat. No. 5,475,763; U.S. Pat. No. 5,554,608; U.S. Pat. No. 5,648,394; U.S. Pat. No. 5,652,273; U.S. Pat. No. 5,674,477; U.S. Pat. No. 5,728,736; U.S. Pat. No. 5,776,442; U.S. Pat. No. 5,824,665; U.S. Pat. No. 5,840,752; U.S. Pat. No. 5,908,867; U.S. Pat. No. 5,939,458; U.S. Pat. No. 5,958,946; U.S. Pat. No. 5,962,466; U.S. Pat. No. 6,020,006; U.S. Pat. No. 6,037,326; U.S. Pat. No. 6,060,471; U.S. Pat. No. 6,093,748; U.S. Pat. No. 6,121,269; U.S. Pat. No. 6,218,435; U.S. Pat. No. 6,235,737; U.S. Pat. No. 6,239,170; U.S. Pat. No. 6,248,751; U.S. Pat. No. 6,299,865; U.S. Pat. No. 6,414,017; U.S. Pat. No. 6,743,419; and U.S. Pat. No. 6,743,822, all of which are incorporated herein by reference.

The concentration of the TRPM8 and/or TRPA1 agonist in the composition may be varied over a wide range up to a saturated solution, preferably from 0.1% to 30% by weight or even more; the reduction of hair growth increases as the amount applied increases per unit area of skin. The maximum amount effectively applied is limited only by the rate of penetration of the skin. The effective amounts may range, for example, from 10 to 3000 micrograms or more per square centimeter of skin.

The vehicle can be inert or can possess cosmetic, physiological and/or pharmaceutical benefits of its own. Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, petroleum jelly, palmitic acid, oleic acid, and myristyl myristate. Solvents include ethyl alcohol, isopropanol, acetone, diethylene glycol, ethylene glycol, dimethyl sulfoxide, and dimethyl formamide.

The composition optionally can include components that enhance the penetration of the TRPM8 and/or TRPA1 agonist into the skin and/or to the site of action. Examples of penetration enhancers include urea, polyoxyethylene ethers (e.g., Brij-30 and Laureth-4), 3-hydroxy-3,7,11-trimethyl-1,6,10-dodecatriene, cis-fatty acids (e.g., oleic acid, palmitoleic acid), acetone, laurocapram, dimethylsulfoxide, 2-pyrrolidone, oleyl alcohol, glyceryl-3-stearate, propan-2-ol, myristic acid isopropyl ester, cholesterol, and propylene glycol. A penetration enhancer can be added, for example, at concentrations of 0.1% to 20% or 0.5% to 5% by weight.

The composition also can be formulated to provide a reservoir within or on the surface of the skin to provide for a continual slow release of the TRPM8 and/or TRPA1 agonist. The composition also may be formulated to evaporate slowly from the skin, allowing the agonist extra time to penetrate the skin.

A cream-based topical composition containing a TRPM8 and/or TRPA1 agonist is prepared by mixing together water and all water soluble components in a mixing vessel-A. The pH is adjusted in a desired range from about 3.5 to 8.0. In order to achieve complete dissolution of ingredients the vessel temperature may be raised to up to 45° C. The selection of pH and temperature will depend on the stability of the TRPM8 and/or TRPA1 agonist. The oil soluble components, except for the preservative and fragrance components, are mixed together in another container (B) and heated to up to 70° C. to melt and mix the components. The heated contents of vessel B are poured into the water phase (container A) with brisk stirring. Mixing is continued for about 20 minutes. The preservative components are added at temperature of about 40° C. Stirring is continued until the temperature reaches about 25° C. to yield a soft cream with a viscosity of 8,000-12,000 cps, or a desired viscosity. The fragrance components are added at about 25° C.-30° C. while the contents are still being mixed and the viscosity has not yet built up to the desired range. If it is desired to increase the viscosity of the resulting emulsion, shear can be applied using a conventional homogenizer, for example a Silverson L4R homogenizer with a square hole high sheer screen. The topical composition can be fabricated by including the active agent in the water phase during the aforedescribed formulation preparation or can be added after the formulation (vehicle) preparation has been completed. The active agent can also be added during any step of the vehicle preparation. The components of the cream formulations are described in the examples below.

Example #1

(Cream)

| INCI Name | W/w (%) |
|---|---|
| DI Water | 61.00-75.00 |
| Active ingredient[a] | 1.00-15.00 |
| Mineral oil | 1.90 |
| Glyceryl stearate | 3.60 |
| PEG 100 Stearate | 3.48 |
| Cetearyl Alcohol | 2.59 |
| Ceteareth-20 | 2.13 |
| Dimethicone, 100 ct | 0.48 |
| Lipidure PMB[b] | 3.00 |
| Advanced Moisture Complex[c] | 5.00 |
| Stearyl alcohol | 1.42 |
| Preservative, fragrance and color pigment | qs |
| Total | 100.00 |

[a]The active ingredient is a TRPM8 and/or TRPA1 agonist.
[b]Polyquartinium-51 (Collaborative Labs, NY).
[c]Glycerin, water, sodium PCA, urea, trehalose, polyqauternium-51, and sodium hyaluronate (Collaborative Labs, NY).

Example #2

Cream

| INCI Name | w/w (%) |
|---|---|
| Active ingredient[a] | 0.5-15.00 |
| Glycerol (Glycerin) | 0-5 |
| Isoceteth-20 | 3-7 |
| Glyceryl isostearate | 1.5-5 |
| Dicaprylyl ether | 3-15 |
| Glyceryl triacetate (triacetin) | 0.5-10 |
| Preservative, fragrance and color pigment | q.s. |
| Water | q.s. to 100.00 |

[a]The active ingredient is a TRPM8 and/or TRPA1 agonist.

Example #3

Cream

| INCI Name | w/w (%) |
|---|---|
| Active ingredient[a] | 0.5-15.00 |
| Glycerol (Glycerin) | 0-5 |
| Isoceteth-20 | 3-7 |
| Glyceryl isostearate | 1.5-5 |
| Dicaprylyl ether | 3-15 |
| 1-dodecyl-2-pyrrolidanone | 0.5-10% |
| Preservative, fragrance and color | q.s. |
| Water | to 100.00 |

[a] The active ingredient is a TRPM8 and/or TRPA1 agonist.

Example #4

Cream

| INCI Name | w/w (%) |
|---|---|
| Water | 70 |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| 1-Dodecyl-2-pyrrolidanone | 1-10 |
| Total | 100.00 |

A TRPM8 and/or TRPA1 agonist is added to the example 4 formulation and mixed until solubilized.

Example #5

Cream

| INCI Name | w/w (%) |
|---|---|
| Water | 70-80 |
| Glyceryl Stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Monocaprylate/caprate (Estol 3601, Uniquema, NJ) | 1-10 |
| Total | 100.00 |

A TRPM8 and/or TRPA1 agonist is added to the example 5 formulation and mixed until solubilized.

Example #6

Cream

| INCI Name | w/w (%) |
|---|---|
| Water | 70-80 |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| cis Fatty acids | 1-10 |
| Total | 100.00 |

A TRPM8 and/or TRPA1 agonist is added to the example 6 formulation and mixed until solubilized.

Example #7

Cream

| INCI Name | w/w (%) |
|---|---|
| Water | 70-80% |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Terpene(s) | 1-10 |
| Total | 100.00 |

A TRPM8 and/or TRPA1 agonist is added to the example 7 formulation and mixed until solubilized.

Example #8

Cream

| INCI Name | w/w (%) |
|---|---|
| Water | 70-80% |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Polyoxyethylene sorbitans (tween) | 1-10 |
| Total | 100.00 |

A TRPM8 and/or TRPA1 agonist is added to the example 8 formulation and mixed until solubilized.

A hydroalcoholic formulation containing a TRPM8 and/or TRPA1 agonist is prepared by mixing the formulation components in a mixing vessel. The pH of the formulation is adjusted to a desired value in the range of 3.5-8.0. The pH adjustment can also be made to cause complete dissolution of the formulation ingredients. In addition, heating can be applied to up to 45° C., or even up to 70° C. depending on the stability of the active in order to achieve dissolution of the formulation ingredients. Several hydroalcoholic formulations are listed below.

Example #9

Hydro-Alcoholic

| INCI Name | w/w (%) |
| --- | --- |
| Water | 48.00-62.50 |
| Active ingredient[a] | 0.5-15.00 |
| Ethanol | 16.00 |
| Propylene glycol | 5.00 |
| Dipropylene glycol | 5.00 |
| Benzyl alcohol | 400 |
| Propylene carbonate | 2.00 |
| Captex-300[b] | 5.00 |
| Total | 100.00 |

[a]The active ingredient is a TRPM8 and/or TRPA1 agonist.
[b]Caprylic/capric triglyceride (Abitec Corp., OH).

Example #10

Hydro-Alcoholic

| INCI Name | w/w (%) |
| --- | --- |
| Water | 53.00-67.9 |
| Active ingredient[a] | 0.1-15.00 |
| Ethanol | 16.00 |
| Propylene glycol | 5.00 |
| Dipropylene glycol dimethyl ether | 5.00 |
| Benzyl alcohol | 4.00 |
| Propylene carbonate | 2.00 |
| Total | 100.00 |

[a]The active ingredient is a TRPM8 and/or TRPA1 agonist.

Example #11

Hydro-Alcoholic

| INCI Name | w/w (%) |
| --- | --- |
| Ethanol (alcohol) | 80 |
| Water | 17.5 |
| Propylene glycol dipelargonate | 2.0 |
| Propylene glycol | 0.5 |
| Total | 100.00 |

A TRPM8 and/or TRPA1 agonist is added to the formulation and mixed until solubilized.

Heating can be performed, for example, using a laser, flashlamp or an Intense Pulse Light (IPL) device. For example, the device can be a Diode laser in the wavelength range of 700-1300 nm (e.g., 810 nm), a Ruby laser at 654 nm, an Alexandrite laser at 755 nm, a Nd:YAG laser at 1064 nm, a Nd:YAG laser in the range of 600-850 nm, a Pulsed Light, Intense Pulsed Light, or a Flash Lamp in the wavelength range of 400-1200 nm, a Fluorescent Pulsed Light at 550, 580, or 615-1200 nm, a Light Emitting Diode (LED) in the wavelength range of 400-700 nm, and an optical (580-980 nm) or Diode (800±25 nm) energy combined with Radio-Frequency electrical energy. The energy output (J/cm2) of the light and photothermal devices can be, for example, from 0.5-50 J/cm2, 2-20 J/cm2, or 1-10 J/cm2. Other laser and light source parameters that effect heating include pulse duration, spot size and repetition rate. The ranges for these parameters depend on the heating device used. The pulse duration can range, for example, from 0.1 ms to up to 500 ms or it can be a continuous wave (CW) as described in U.S. Pat. No. 6,273,884.

During heating, the temperature of the skin generally is heated to at least 40° C., for example, between 40° C. and 55° C. However, the skin can be heated, as high as, for example, 70° C. using short millisecond pulses, and avoiding skin burn. For the lower temperature range of 40-60° C., one should keep the exposure time to between 0.5 min to several minutes. For temperatures above 60° C., one should stay within exposure time of 1-500 msec. The temperature of the skin obtained by heating by a particular mechanism generally can be determined as follows. A subject having a normal body temperature is placed in a room having a temperature of 25° C. A 0.009-inch-diameter thermocouple is placed in an area in the skin. The thermocouple output is connected to a National Instruments SCXI-1112 thermocouple signal conditioner. A National Instruments 6052E data acquisition board, having a maximum acquisition rate of 333 kilo-samples per second controlled the data acquisition and signal gain. The SCXI-1112 and NI 6052E DAQ combination could simultaneously detect up to eight thermocouple outputs at a rate of 42 kilo-samples per second. The sampling rate can be conducted, for example, at 1000 samples/sec.

A similar method is used to determine the temperature range in the hypodermal region. In this case, a thermocouple is inserted to a depth of about 5 mm in an ex-vivo human skin and treatment is applied at the skin surface.

The composition should be applied topically to a selected area of skin from which it is desired to reduce hair growth. The time period for the topical composition application, before or after, the heating treatment may vary from as short as 1 day or even a simultaneous application, depending on the nature of the active chemical in the topical composition. Preferably, the composition is applied (multiple, for example, two, three, or four times) within seven days of heating, and more preferably at least once within one or two days of heating. Compositions can be applied once a day for at least two or three days prior to heating.

The composition, for example, can be applied to the face, particularly to the beard area of the face, i.e., the cheek, neck, upper lip, and chin. The composition can also be applied to the legs, arms, torso, axillae, eyebrows, and/or bikini area. The composition is particularly suitable for reducing the growth of unwanted hair in women having hirsutism or other conditions. The composition/heating combination may be used as an adjunct to other methods of hair removal, including shaving, waxing, mechanical epilation, chemical depilation, and electrolysis. For example, TRPM8 and/or TRPA1 agonist(s), can be used in combination with any of the aforesaid other methods of hair removal, e.g., waxing. Such combination treatment can further include a heat depilatory treatment (e.g., laser). Any combination and/or sequence of the aforesaid treatments with a TRPM8 and/or TRPA1 agonist(s) is within the scope of the invention.

Reduced hair growth can be demonstrated quantitatively by reduced hair length, hair diameter, hair pigmentation, and/or hair density in the treated area. Reduced hair growth can be demonstrated cosmetically by less visible hair, shorter hair stubble, finer/thinner hair, softer hair, and/or a longer-lasting shave in the treated area.

The protocols used in the appended Examples are set forth below.

Human Hair Follicle Growth Assay

Human hair follicles in growth phase (anagen) were isolated from face-lift tissue (obtained from plastic surgeons). The skin was sliced into thin strips exposing 2-3 rows of follicles that could readily be dissected. Follicles were placed into William's E medium (Life Technologies, Gaithersburg, Md.) supplemented with 2 mM L-glutamine, 10 □g/ml insulin, 10 ng/ml hydrocortisone, and an antibiotic/antimicotic mixture as described in Philpott et al. (1990) *J. Cell Sci.* 97 (Pt3):463-71. The follicles were incubated in 24-well plates (1 follicle/well) at 37° C. in an atmosphere of 5% $CO_2$ and 100% humidity for different periods of time (Philpott et al. (1990) supra). The length of hair follicle was assessed using an image analysis software system. To determine the effect of molecules modulating TRPM8/TRPA1 activity on hair growth, hair follicles were incubated with icilin (Tocris Bioscience) and L-Menthol, L-menthyl lactate (Sigma). Hair follicle images were taken in the 24-well plates under the dissecting scope under a power of 20×. Hair follicle length was measured on day 0 (day follicles were placed in culture) and again on day 6. The growth of hair fiber was calculated by the subtracting the follicle length on day 0 from that determined on day 6.

Immunohistochemistry

To determine TRPM8 expression in the hair follicle indirect immunofluorescence protocol was employed. Cryostat sections (8 □m) of hair follicles were freshly prepared and fixed in acetone, and preincubated with 10% goat normal serum, followed by an incubation with the primary antibody against TRPM8 (1:50; Novus-Biologicals) overnight at room temperature. Sections were then incubated with TRITC-labeled goat ant-rabbit IgG (Jackson ImmunoResearch; 45 min, 37° C.).

For detection of proliferating cells the indirect immunofluorescence protocol using rabbit monoclonal antibody against Ki-67. Eight □m hair follicle sections were fixed in formalin and postfixed in ethanol/acetic acid. Next, the sections were incubated with antibody against Ki-67 (1:50; Dako; M 7187) overnight at room temperature, followed by incubation with TRITC-labeled goat ant-rabbit IgG (Jackson ImmunoResearch; 45 min, 37° C.).

Counterstaining was performed using HOECHST 33342 dye (10 mg/ml in PBS; 10 minutes). Each phase was interspersed by a washing step (three times) in PBS. Finally, sections were mounted using VectaShield Vector Laboratories).

For the immunodetection of melanogenic proteins, sections were incubated with either mouse monoclonal antibody against human tyrosinase or chicken monoclonal antibody against human p-mel 17 (Neomarker and Zymed, respectively; 1:100, overnight), followed by incubation with TRITC-labeled goat anti-rabbit IgG (Jackson ImmunoResearch; 45 min, 37° C.) and FITC-labeled goat anti-chicken IgG, respectively. Next, sections were counterstained with Hoechst 33342 (1:300, 15 min) for identification of cell nuclei, and mounted using VectaShield (Vector Laboratories).

All sections were examined under a Olympus BX 60 fluorescent microscope and photodocumented with the help of a digital image analysis system (CoolSnap™ cooled CCD camera, Alpha Innotech)

Western Blot Analysis

Total cellular proteins of human melanocytes were harvested in a lysis buffer (Total protein extraction kit; CHEMICON International, Inc). Twenty □g protein were loaded per lane, separated by 10% sodium dodecyl sulfate polyacrylamide gel electrophoresis, and transferred to nitrocellulose membrane at 100 V for 1 h. Following overnight blocking with 5% nonfat dry milk/bovine serum albumin (BSA) in Tris-phosphate-buffered saline (PBS) (0.5% Tween-20 in PBS) at 4° C., the membrane was incubated overnight with a monoclonal antibody against either tyrosinase or tyrosinase-related protein-1 or actin at a dilution of 1:1000. After incubation, the membrane was briefly washed in PBS, then three times with Tris-PBS, and incubated with corresponding secondary antibody at 1:1000 dilution (Pierce, Rockford, Ill.) in 1% milk/0.2% BSA for 1 hour. After extensive washing the membrane was incubated for 1 min with the enzyme-linked chemiluminescence Western Blotting Detection Reagent (Amersham, Buckinghamshire, U.K.), and bands were detected on preflashed Kodak X-Omat film and developed after several seconds of exposure.

RT-PCR

TRPA1 gene transcription in full-thickness human skin and in isolated dermal papilla cells of the hair follicle was characterized by RT-PCR analysis. Total RNA was isolated from full-thickness scalp skin samples and isolated hair follicle dermal papilla cells by using TRIzol reagent (Invitrogen, San Diego, Calif.). cDNA was synthesized by reverse transcription of 2.5 µg total RNA, using a SuperScript™ First-Strand Synthesis System for RT-PCR (Invitrogen, San Diego, Calif.). The following sets of oligonucleotide primers were used to amplify specific c-DNA: human TRPA1: Primers#1: 5'-TCATGGTCCAACAGAACACATGGC-3' SEQ NO ID: 1 and 5'-GCATGACAGGCATGGTACAGTGTT-3' SEQ NO ID: 2 (Primer Product Size: 228 bp), Primers#2: 5'-TCCTCTCCATCTGGCAGCAAAGAA-3' SEQ NO ID: 3 and 5'-ATTGTGGCTCAGAAGAAGCGCAAC-3' SEQ NO ID: 4 (Primer Product Size: 262 bp). Amplification was performed using PCR SuperMix (Invitrogen) over 38 cycles, using an automated thermal cycler. Each cycle consisted of the following steps: denaturating at 94° C. (1 mm), annealing at 58° C. (45 s), and extension at 72° C. (45 s). PCR products were analyzed by gel electrophoresis (2% agarose) and enzymatic digestion using standard methods.

Example 1

Immunohistochemical Localization of TRPM8 in Anagen Hair Follicles

To localize TRPM8 in the human anagen hair follicle, immunohistochemistry was applied by using rabbit polyclonal antibody against human TRPM8. Expression of TRPM8 was found in the dermal papilla of the hair follicle, as well as in the cells of the hair matrix surrounding the dermal papilla. Double immunostaining for simultaneous detection of TRPM8 and melanocyte marker pMel-17 (gp 100) revealed co-localization of these two proteins in the hair follicle. This suggests that the TRPM8-expressing cells seen in the hair matrix are melanocytes. Thus, TRPM8 expression was detected in the dermal papilla of the hair follicle, and in the follicular and epidermal melanocytes.

Example 2

Expression of TRPA1 mRNA in Human Skin and Hair Follicle

TRPA1 gene transcription in full-thickness human skin and in isolated dermal papilla cells of the hair follicle was characterized by RT-PCR analysis. Total RNA from human scalp skin and from hair follicle dermal papilla cells were extracted and reverse transcribed. As a result, the detectable steady-state levels of TRPA1-mRNA were found in the skin as well as in the dermal papilla cells.

Example 3

Effect of TRPM8 and TRPA1 Agonists on Hair Growth

To identify whether modulation of TRPM8 and TRPA1 activity could affect hair growth, their agonists were tested in the hair follicle culture model. Hair follicle treatment with 10 uM of menthol, icilin, and menthyl lactate, caused statistically significant hair growth inhibition by 40%, 45% and 60% respectively, compared to the control. Hair follicle treatment with icilin (an agonist of TRPM8 and TRPA1) resulted in inhibition of cell proliferation in a concentration-dependent manner, which was detected by a prominent decrease in Ki-67 immunoreactivity in the hair matrix and in the outer root sheath. Thus, activation of either TRPM8 or TRPA1 by a cooling agent leads to a significant reduction of hair growth rate in vitro.

Example 4

Effect of TRPM8 and TRPA1 Agonists on Melanocytes

To determine whether a TRPM8 and TRPA1 agonist can affect pigment producing activity of the melanocytes, expression of tyrosinase was analyzed in the hair follicles treated with 10 uM icilin by immunohistochemistry. Tyrosinase expression was decreased in treated hair follicles, compared to the control. In addition, the effects of icilin on melanogenic protein expression were tested in human epidermal melanocytes culture. A decrease in tyrosinase and tyrosinase-related protein (TRP)-1 expression levels were observed 48 hours after 10 uM icilin treatment, compared to the control, as determined by Western blot analysis. Therefore, icilin exerts hair growth inhibitory effect in vitro, accompanied by a decrease in pigment producing activity of the melanocytes. These results suggest that agonists of TRPM8 and TRPA1 receptors may protect melanocytes from overpigmentation.

Other embodiments are within the claims. For example, the classes of compounds and specific compounds described in the list of patents above and incorporated by reference can be used in the methods disclosed in the Summary section.

All documents cited in the Detailed Description are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing human hair growth, comprising:
   selecting an area of skin from which reduced hair growth is desired, and
   applying to the area of skin, in an amount effective to reduce hair growth, a composition comprising a TRPM8 agonist as the only active hair growth inhibitor and a dermatologically acceptable vehicle; wherein if the TRPM8 agonist is a terpene, then it is a cyclic terpene; and
   wherein said selecting and applying is performed multiple times in a seven day period.

2. The method of claim 1, wherein the TPRM8 agonist is a cyclic terpene.

3. The method of claim 2, wherein the cyclic terpene is menthol or menthyl lactate.

4. The method of claim 1, wherein the composition includes between 0.1% and 30% of the agonist by weight.

5. The method of claim 1, wherein the area of skin of a human selected from the group consisting of the face, axillae, legs, eyebrows, and bikini area.

6. The method of claim 1, wherein the TRPM8 agonist is icilin.

7. The method of claim 1, wherein the TPRM8 agonist is eucalyptol, menthone, cineole, terpineol, D-limonene, isopulegol, carvacol, trans-p-menthane-3,8-diol, cis-p-menthane-3,8-diol, L-carvone, N-ethyl paramenthane-3-carboxamide, menthone glycerin acetal, menthoxypropanediol, monomenthylsuccinate, or monomenthyl glutarate.

8. The method of claim 1, wherein said selecting and applying are performed two, three, or four times during a seven day period.

9. The method of claim 1, wherein the TRPM8 agonist is a compound of formula:

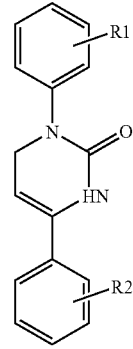

wherein:

R1 is selected from hydroxyl, chloro, fluoro, $C_{2-4}$ alkyl, acetoxy, and trifluoromethyl; and R2 is selected from nitro, chloro, fluoro, $C_{2-4}$ alkyl, and trifluoromethyl.

10. The method of claim 1, wherein the TRPM8 agonist is eugenol.

11. A method of reducing human hair growth, comprising
   selecting an area of skin from which reduced hair growth is desired, and
   applying to the area of skin, in an amount effective to reduce hair growth, a composition comprising a TRPM8 agonist as the only active hair growth inhibitor and a dermatologically acceptable vehicle; wherein when the TRPM8 agonist is a terpene, it is a cyclic terpene; and wherein the area of skin is not further contacted with a heat depilatory, waxing, mechanical epilation, or electrolysis within one day of the applying.

12. The method of claim 11, wherein said composition is applied multiple times during a seven day period.

13. The method of claim 11, wherein the TPRM8 agonist is a cyclic terpene.

14. The method of claim 13, wherein the cyclic terpene is menthol or menthyl lactate.

15. The method of claim 11, wherein the TPRM8 agonist is eucalyptol, menthone, cineole, terpineol, D-limonene, isopulegol, carvacol, trans-p-menthane-3,8-diol, cis-p-menthane-3,8-diol, L-carvone, N-ethyl paramenthane-3-carboxamide, menthone glycerin acetal, menthoxypropanediol, monomenthylsuccinate, or monomenthyl glutarate.

16. The method of claim 11, wherein the composition includes between 0.1% and 30% of the agonist by weight.

17. The method of claim 11, wherein the area of skin of a human selected from the group consisting of the face, axillae, legs, eyebrows, and bikini area.

18. The method of 11, wherein the TRPM8 agonist is a compound of formula:

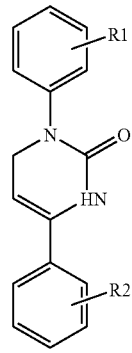

wherein:
R1 is selected from hydroxyl, chloro, fluoro, $C_{2-4}$ alkyl, acetoxy, and trifluoromethyl; and
R2 is selected from nitro, chloro, fluoro, $C_{2-4}$ alkyl, and trifluoromethyl.

19. The method of claim 11, wherein the TRPM8 agonist is icilin.

20. The method of claim 11, wherein the TRPM8 agonist is eugenol.

* * * * *

UNITED STATES PATENT AND TRADEMARK OFFICE
CERTIFICATE OF CORRECTION

PATENT NO. : 7,727,516 B2
APPLICATION NO. : 11/709616
DATED : June 1, 2010
INVENTOR(S) : Natalia Botchkareva and Douglas Shander It is certified that error appears in the above-identified patent and that said Letters Patent is hereby corrected as shown below:

In Col. 15, line 57, Claim 7, delete "carvacol," and insert --carvacrol,--, therefor.

In Col. 17, line 13, Claim 15, delete "carvacol," and insert --carvacrol,--, therefor.

Signed and Sealed this

Fourteenth Day of September, 2010

David J. Kappos
*Director of the United States Patent and Trademark Office*